United States Patent [19]

Bright et al.

[11] Patent Number: 5,041,596

[45] Date of Patent: Aug. 20, 1991

[54] FORMATION OF GLYCOL BISPHOSPHATE COMPOUNDS

[75] Inventors: Danielle A. Bright, Spring Valley; Alan M. Aaronson, Flushing Meadows, both of N.Y.

[73] Assignee: Akzo America Inc., New York, N.Y.

[21] Appl. No.: 374,719

[22] Filed: Jul. 3, 1989

[51] Int. Cl.$^5$ .............................. C07C 9/62
[52] U.S. Cl. ....................... 558/91; 558/89; 558/163
[58] Field of Search ............... 558/91, 163, 89

[56] References Cited

U.S. PATENT DOCUMENTS

| | | | |
|---|---|---|---|
| 3,324,205 | 6/1967 | Carpenter et al. | 558/91 |
| 3,492,373 | 1/1970 | Matson et al. | 558/162 |
| 3,810,961 | 5/1974 | Pivawer | 558/91 |
| 3,869,526 | 3/1975 | Combey et al. | 558/162 |
| 4,289,712 | 9/1981 | Turley | 558/91 |
| 4,496,494 | 1/1985 | Pamloski et al. | 558/91 |

FOREIGN PATENT DOCUMENTS 272484  6/1988  European Pat. Off. .............. 558/91

40392  4/1974  Japan .

OTHER PUBLICATIONS

Chuuilin et al., Chem. Abst., 104-109787d, (1986).
Hata et al., Chem. Abst., vol. 81, 136919, (1974).
Toy, J.A.C.S., vol. 70, pp. 3882-3886, (1948).
Toy, J.A.C.S., vol. 71, pp. 2268, (1949).
Weil et al., Journal of Fire Retardant Chemistry, vol. 9, (Feb. 1982), p. 39.
Annakutty et al., Chem. Abst., 108-205647m, (1988).
Dhawan et al., Chem. Abst., 101-171359g, (1984).
Kyodo Chem. Co. Ltd., Chem. Abst., 95-186842r, (1981), Gazizov et al., Chem. Abst., 92-59295c, (1980).

*Primary Examiner*—Cecilia Shen
*Attorney, Agent, or Firm*—Richard P. Fennelly; Louis A. Morris

[57] ABSTRACT

Glycol bisphosphate compounds are formed by first hydrolytically condensing a dihydrocarbylhalophosphate to form a tetrahyrocarbyl pyrophosphate and then reacting the pyrophosphate with a cyclic ether to form the glycol bisphosphate.

12 Claims, No Drawings

FORMATION OF GLYCOL BISPHOSPHATE COMPOUNDS

BACKGROUND OF THE INVENTION

1. Field of the Invention

The present invention is a novel process for forming glycol bisphosphate compounds.

2. Description of the Prior Art

Glycol bisphosphate compounds are a known class of organophosphorus compounds which are useful, for example, as flame retardants in polymers. These compounds have the general formula

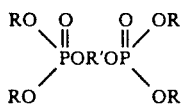

where R is hydrocarbyl (e.g., alkyl, aryl, alkaryl, arylalkyl, etc.) and R' is hydrocarbylene (e.g., alkylene, arylene, etc ). For example, R can be phenyl with R' being alkylene, such as ethylene, isopropylene, neopentyl, etc.

This class of compounds may be prepared by reacting a dihydrocarbylhalophosphate (e.g., diphenylchlorophosphate) with a glycol in the presence of an amine as described in Biorg. Khim., 11(6) 845-848 (1985). However, such a route needs to be run at relatively low temperatures (0°-10° C.) in order to achieve good yields. If this reaction is run at room temperature, it has been found that the major product is triphenylphosphate. This reaction also use equimolar amounts of amine which produces an amine salt which must be filtered from the reaction mixture. Also, a solvent is needed in such a process.

Another approach to making glycol bisphosphate compounds is described in Japanese Patent Publication No. 74 40342 which shows reaction of phosphorus oxytrichloride with a glycol followed by reaction with phenol.

U.S. Pat. No. 3,492,373 teaches condensation of a bisphenol or bisphenol alkane with a monophenol, a phenylphosphorous halide, or a mixture of phenylphosphorous halide and monophenol.

M. Combey et al in U.S. Pat. No. 3,869,526 speak of formation of bis(phosphates) by one of two methods. The first involves reaction of an alcohol, phenol or both with phosphorus oxychloride and a diol in that order. The second involves transesterification of a triorganophosphate with a diol, polyol or diphenol preferably in the presence of a metallic transesterification catalyst.

SUMMARY OF THE INVENTION

The instant process, in one embodiment, is a two step procedure for forming glycol bisphosphates. The first step involves the hydrolytic condensation of a dihydrocarbylhalophosphate to form a tetrahydrocarbyl pyrophosphate. The second step involves reaction of the pyrophosphate with a cyclic ether to form the desired glycol bisphosphate.

Another embodiment of the invention is the reaction of the pyrophosphate with cyclic ether to form the bisphosphate.

Additionally, it is deemed that the first step of preparing the pyrophosphate compound by hydrolytic condensation of a diarylhalophosphate is novel and another aspect of the instant invention.

DETAILED DESCRIPTION OF THE INVENTION

The hydrolytic condensation of the dihydrocarbylhalophosphate involves reaction of water with a compound of the formula

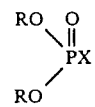

where R is hydrocarbyl (independently alkyl, aryl, alkaryl, arylalkyl, etc.) and X is halogen. The foregoing hydrocarbyl moieties can either be unsubstituted or can be substituted with non-interfering substituents to the instant reaction (e.g., halogen). This can be practiced at temperatures of from about 50° C. to about 170° C. and results in formation of a pyrophosphate compound of the formula

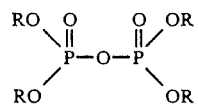

where R has the meaning given above. R can be substituted or unsubstituted phenyl, if desired. Examples of substituted phenyl groups R in the foregoing formula include xylyl, 2,6-dichlorophenyl, 4-tert-butylphenyl, 2,3,4,5,6-pentachlorophenyl, 4-(1,3-dimethylbutyl)phenyl, 3-methylphenyl, 4-chlorophenyl, 3-nitrophenyl, 4-nitrophenyl, and the like. The hydrolytic condensation of dialkylhalophosphates is known (see J. Amer. Chem. Soc. Vol. 70, 3882-3886 and Vol. 71, 2268).

In order to achieve the insertion of the desired hydrocarbyl bridging group between the two phosphate moieties in the pyrophosphate, that compound is then reacted with a cyclic ether. The cyclic ether can be of the formula

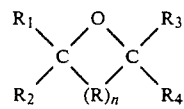

where each of $R_1$-$R_4$ are independently hydrogen or substituted or unsubstituted alkyl or aryl, R is substituted or unsubstituted alkylene, and n is an integer of from 0 to 1. Representative ethers which can be used include ethylene oxide, propylene oxide, epichlorohydrin, epibromohydrin, cyclohexene oxide, epoxidized soybean oil, oxetane, 3,3-dimethyloxetane, 3,3-bis(chloromethyl)oxetane, 3,3-bis(bromomethyl)oxetane, the diglycidyl ether of bisphenol A, the brominated diglycidyl ether or bisphenol A, and the like. The reaction of the pyrophosphate with the cyclic ether can be conducted at temperatures of from about 30° C. to about 160° C. using molar ratios of pyrophosphate to ether ranging from about 1:1 to about 1:2. Advantageously, a catalytically effective amount (e.g., from about 0.1% to about 2%, by weight, based on the weight of the pyrophosphate) of amine or Lewis acid catalyst is used to accelerate the reaction.

The following Examples further illustrate the instant invention.

EXAMPLE 1

This Example illustrates the preparation of tetraphenyl pyrophosphate.

To 10 moles of diphenylchlorophosphate (2686 gm) heated to 70° C. under nitrogen, was added 5 moles (90 gm) of water over a period of five hours. The temperature was kept at 75° C. throughout the addition. At the end of the addition period, the reaction mixture was kept at 75°-80° C. for one hour, and the temperature was then raised and maintained at 120° C. for three hours. It was then raised to 140° C. and maintained at that temperature for an additional three hours. A reddish orange oil (2430 gm, 98.7% yield) was obtained and assayed at 96% purity by $^{31}P$ nmr.

EXAMPLE 2

Ethylene glycol bis (diphenyl phosphate) was made by the following procedure. To the tetraphenyl pyrophosphate from Example 1 (0.5 mole, 243 gm) was added 2 ml of pyridine. This mixture was heated to 70° C. under nitrogen. Ethylene oxide (43 gm, 0.98 mole) was slowly fed into the resulting mixture at 70° C. over ten hours. At the end of this time, the excess ethylene oxide was removed by applying slight vacuum. The reaction mixture was washed at 60° C. with 200 ml of 2% sulfuric acid, followed by 200 ml of 2% sodium hydroxide and two aliquots of 200 ml of water. Traces of water were removed at 100° C. under vacuum. The viscous yellow oil that remained (224.6 gm, 87.4% yield) was analyzed. On standing, the oil solidified (mp =38°-40° C.). The hydrogen and $^{31}P$ nmr analysis was consistent with the proposed structure. The material assayed at 97.2% by high pressure liquid chromatography.

EXAMPLE 3

This Example illustrates the preparation of propylene glycol bis (diphenyl phosphate). To the tetraphenyl pyrophosphate from Example 1 (0.5 mole, 243 gm), that had been heated to 70° C. under nitrogen, was added a solution of 32 gm (0.55 mole) of propylene oxide and 3 ml of pyridine over a period of three hours. The reaction mixture was kept at 70° C. for six hours. Excess propylene oxide was distilled from the reaction mixture. After washing and drying, as described in Example 2, there was left 218 gm of a colorless oil (80% yield). The anticipated identity of the product was confirmed by $^1H$ and $^{31}P$ nmr and the material assayed at 96.7% purity by $^{31}P$ nmr.

EXAMPLE 4

Neopentyl glycol bis (diphenyl phosphate), as claimed in U.S. Ser. No. 07/374,716, entitled "Novel Aromatic Bisphosphates" was made by this Example. To tetraphenyl pyrophosphate from Example 1 (0.5 mole, 243 gm), heated to 80° C. under nitrogen, was added a solution of 3,3-dimethyl oxetane (0.5 mole, 43.1 gm) and 2 ml of pyridine. The temperature was raised to 120° C. and was kept at constant temperature for ten hours. After washing and drying as described in Example 2, there was obtained 253.5 gm of a light yellow oil (89% yield). The identify of the product was confirmed by $^1H$ and $^{31}P$ nmr, and this material assayed at 92% purity by $^{31}P$ nmr.

EXAMPLE 5

Dichloroneopentyl glycol bis (diphenyl phosphate), as also claimed in U.S. Ser. No. 07/371,716, was made in this Example. It was made as described in Example 4 from 0.32 mole, 154.2 gm of tetraphenyl pyrophosphate, 0.32 mole (50 gm) of 3,3-bis(chloromethyl) oxetane and 2 ml of pyridine. A viscous light brown oil (152.4 gm) was obtained at 75% yield. The identity of the product was confirmed by $^1H$ nmr.

EXAMPLE 6

Propylene glycol bis(diphenylphosphate) was made in this Example. To 0.5 mole of tetraphenylpyrophosphate (243 grams) was added 0.2 grams of magnesium chloride. The mixture was heated to 80° C. Propylene oxide (50 ml) was slowly added over six hours with the temperature being kept at 80° C. After the addition was completed, the reaction mixture was heated to 85° C. for an additional four hours. It was then washed at 50° C. with 200 ml of 2% sulfuric acid, 200 ml of 2% sodium hydroxide, and two 200 ml portions of water. After removal of traces of water at vacuum at 90° C., there was left 218 grams (80.7% yield) of a colorless oil which, by $^{31}P$ nmr analysis, was shown to contain 84% of the desired bisphosphate and 14% of triphenylphosphate by-product.

EXAMPLE 7

Example 6 was repeated using stannous octoate as a catalyst (at 0.3% by weight of tetraphenylpyrophosphate) and ethylene oxide in place of propylene oxide in order to produce ethylene glycol bis(diphenylphosphate). The results were comparable to those achieved in Example 6.

The foregoing Examples have been presented to illustrate certain embodiments of the instant invention and, for this reason, should not be construed in a limiting sense. The scope of protection that is sought is set forth in the claims which follow.

We claim:

1. A process for the formation of a glycol bisphosphate which comprises:
   (a) hydrolytic condensation of a dihydrocarbylhalophosphate to form a tetrahydrocarbyl pyrophosphate, and
   (b) reaction of the tetrahydrocarbyl pyrophosphate with a cyclic ether to form the glycol bisphosphate.

2. A process as claimed in claim 1 wherein the dihydrocarbylhalophosphate is a diarylhalophosphate of the formula

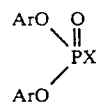

where Ar is an aryl moiety and X is halo.

3. A process as claimed in claim 1 wherein the cyclic ether is of the formula

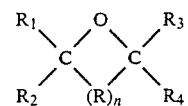

where each of $R_1$-$R_4$ are independently hydrogen or substituted or unsubstituted alkyl, R is substituted or unsubstituted alkylene, and n is an integer of from 0 to 1.

4. A process for the formation of a glycol bisphosphate which comprises:
    (a) hydrolytic condensation of a dihydrocarbylhalophosphate of the formula

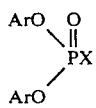

where Ar is an aryl moiety and X is halo to form a tetrahydrocarbyl pyrophosphate, and
    (b) reaction of the tetrahydrocarbyl pyrophosphate with a cyclic ether to form the glycol bisphosphate wherein the condensation is conducted at a temperature of from about 50° C. to about 170° C.

5. A process for the formation of a glycol bisphosphate which comprises:
    (a) hydrolytic condensation of a dihydrocarbylhalophosphate to form a tetrahydrocarbyl pyrophosphate, and
    (b) reaction of the tetrahydrocarbyl pyrophosphate with a cyclic ether of the formula

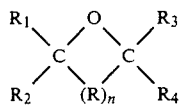

where each of $R_1$-$R_4$ are independently hydrogen or substituted or unsubstituted alkyl, R is substituted or unsubstituted alkylene, and n is an integer of from 0 to 1 to form the glycol bisphosphate wherein the cyclic ether is reacted at a temperature of from about 30° C. to about 160° C.

6. A process for the formation of a glycol bisphosphate which comprises:
    (a) hydrolytic condensation of a dihydrocarbylhalophosphate to form a tetrahydrocarbyl pyrophosphate, and
    (b) reaction of the tetrahydrocarbyl pyrophosphate with a cyclic ether to form the glycol bisphosphate wherein the condensation reaction (a) is conducted at a temperature of from about 50° C. to about 170° C. and the reaction (b) of the cyclic ether is conducted at a temperature of from about 30° C. to about 160° C.

7. A process as claimed in claim 6 wherein the reaction (b) is effected in the presence of a catalytically effective amount of amine or Lewis acid catalyst.

8. A process for the formation of a glycol bisphosphate which comprises the reaction of a tetrahydropyrophosphate with a cyclic ether.

9. A process as claimed in claim 8 wherein the tetrahydropyrophosphate is of the formula

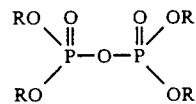

where R is hydrocarbyl.

10. A process as claimed in claim 9 wherein the tetrahydropyrophosphate is reacted with a cyclic ether of the formula

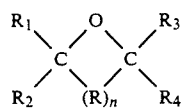

where each of $R_1$-$R_4$ are independently hydrogen or substituted or unsubstituted alkyl or aryl, R is substituted or unsubstituted alkylene, and n is an integer of from about 0 to about 1 and the reaction is carried out at a temperature of from about 30° C. to about 160° C.

11. A process for the formation of a glycol bisphosphate which comprises the reaction of a tetrahydropyrophosphate with a cyclic ether wherein the reaction is conducted at a temperature of from about 30° C. to about 160° C. using a molar ratio of pyrophosphate to ether ranging from about 1:1 to about 1:2.

12. A process for the formation of a glycol bisphosphate which comprises the reaction of a tetrahydropyrophosphate with a cyclic ether which comprises use of a catalytically effective amount of an amine or Lewis acid catalyst.

* * * * *